US009248175B2

(12) United States Patent
Klumpp et al.

(10) Patent No.: US 9,248,175 B2
(45) Date of Patent: Feb. 2, 2016

(54) LIVE-ATTENUATED COMPOSITIONS FOR BACTERIAL INFECTIONS (71) Applicant: Northwestern University, Evanston, IL (US)

(72) Inventors: David Klumpp, Chicago, IL (US); Anthony Schaeffer, Hinsdale, IL (US); Benjamin Billips, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 14/263,276

(22) Filed: Apr. 28, 2014

(65) Prior Publication Data
US 2014/0234369 A1 Aug. 21, 2014

Related U.S. Application Data (63) Continuation of application No. 13/266,346, filed as application No. PCT/US2010/034892 on May 14, 2010, now Pat. No. 8,709,444.

(60) Provisional application No. 61/178,384, filed on May 14, 2009.

(51) Int. Cl.
*A61K 39/108* (2006.01)
*C12N 1/20* (2006.01)
*A61K 35/74* (2015.01)
*A61K 35/744* (2015.01)

(52) U.S. Cl.
CPC ............ *A61K 39/0258* (2013.01); *A61K 35/74* (2013.01); *A61K 35/744* (2013.01)

(58) Field of Classification Search
CPC . A61K 35/74; A61K 35/744; A61K 39/0258; C12N 15/70
USPC ............. 424/257.1, 94.61; 435/252.33, 252.8
See application file for complete search history.

(56) References Cited

U.S. PATENT DOCUMENTS

| 5,066,596 | A | 11/1991 | Manning et al. |
| 2003/0124634 | A1 | 7/2003 | Lam et al. |
| 2006/0233829 | A1 | 10/2006 | Curtiss, III |
| 2007/0218079 | A1 | 9/2007 | Patzel |

OTHER PUBLICATIONS

Carroll et al 2004 (Veterinary Microbiology 102 (2004) 73-85).*
Billips et al (Journal of Urology, (Apr. 2009) vol. 181, No. 4, Suppl.S, pp. 235-236).*
Alteri & Mobley, "Quantitative profile of the uropathogenic *Escherichia coli* outer membrane proteome during growth in human urine," Infect Immun, 75: 2679-2688, 2007.
Anderson et al., "Intracellular bacterial biofilm-like pods in urinary tract infections," Science, 301: 105-107, 2003.
Backhed et al., "Induction of innate immune responses by *Escherichia coli* and purified lipopolysaccharide correlate with organ- and cell-specific expression of Toll-like receptors within the human urinary tract," Cell Microbiol, 3: 153-158, 2001.
Backhed et al., "Structural requirements for TLR4-mediated LPS signalling: a biological role for LPS modifications," Microbes Infect, 5:1057-1063, 2003.
Barrangou et al., "CRISPR provides acquired resistance against viruses in prokaryotes," Science, 315: 1709-1712, 2007.
Bhushan et al., "Uropathogenic *Escherichia coli* block MyD88-dependent and activate MyD88-independent signaling pathways in rat testicular cells," J Immunol, 180: 5537-5547, 2008.
Billips et al., "Modulation of host innate immune response in the bladder by uropathogenic *Escherichia coli*," Infect Immun, 75: 5353-5360, 2007.
Billips et al., "Molecular basis of uropathogenic *Escherichia coli* evasion of the innate immune response in the bladder," Infect Immun, 76(9): 3891-3900, 2008.
Blattner et al., "The complete genome sequence of *Escherichia coli* K-12," Science, 277: 1453-1462, 1997.
Cirl et al., "Subversion of Toll-like receptor signaling by a unique family of bacterial Toll/interleukin-1 receptor domain-containing proteins," Nat Med, 14: 399-406, 2008.
Folkesson et al., "Components of the peptidoglycan-recycling pathway modulate invasion and intracellular survival of *Salmonella enterica* serovar Typhimurium," Cell Microbiol, 7: 147-155, 2005.
Foxman & Brown, "Epidemiology of urinary tract infections: transmission and risk factors, incidence, and costs," Infect Dis Clin North Am, 17: 227-241, 2003.
Foxman, "Epidemiology of urinary tract infections: incidence, morbidity, and economic costs," Am J Med, 113 (Suppl 1A): 5S-13S, 2002.
Garofalo et al., "*Escherichia coli* from urine of female patients with urinary tract infections is competent for intracellular bacterial community formation," Infect Immun, 75: 52-60, 2007.
Goluszko et al., "Vaccination with purified Dr Fimbriae reduces mortality associated with chronic urinary tract infection due to *Escherichia coli* bearing Dr adhesin," Infect Immun, 73: 627-631, 2005.
Grischke et al., "Treatment of bacterial infections of the female urinary tract by immunization of the patients," Urol Int, 42: 338-341, 1987.
Hilbert et al., "Uropathogenic *Escherichia coli* dominantly suppress the innate immune response of bladder epithelial cells by a lipopolysaccharide- and Toll-like receptor 4-independent pathway," Microbes Infect, 10: 114-121, 2008.

(Continued)

*Primary Examiner* — Padma V Baskar
(74) *Attorney, Agent, or Firm* — Casimir Jones, S.C.; Jason Bond (57) ABSTRACT

The present invention relates to compositions and methods for disease treatment and prevention through administration of a live attenuated composition. In particular, the present invention provides compositions and methods for the treatment and prevention of urinary tract infection by administration of a live attenuated compositions lacking O-antigen ligase activity.

4 Claims, 4 Drawing Sheets

(56) References Cited

OTHER PUBLICATIONS

Hopkins et al., "Vaginal mucosal vaccine for recurrent urinary tract infections in women: results of a phase 2 clinical trial," J Urol, 177: 1349-1353; quiz 1591, 2007.

Hull et al., "Role of type 1 fimbria- and P fimbria-specific adherence in colonization of the neurogenic human bladder by *Escherichia coli*," Infect Immun, 70: 6481-6484, 2002.

Hultgren et al., "Regulation of production of type 1 pili among urinary tract isolates of *Escherichia coli*," Infect Immun, 54: 613-620, 1986.

Hunstad et al., "Suppression of bladder epithelial cytokine responses by uropathogenic *Escherichia coli*," Infect Immun, 73: 3999-4006, 2005.

Johnson et al., "Clonal relationships and extended virulence genotypes among *Escherichia coli* isolates from women with a first or recurrent episode of cystitis," J Infect Dis, 183: 1508-1517, 2001.

Johnson et al., "Phylogenetic and pathotypic similarities between *Escherichia coli* isolates from urinary tract infections in dogs and extraintestinal infections in humans," J Infect Dis, 183: 897-906, 2001.

Johnson et al., "Phylogenetic relationships among clonal groups of extraintestinal pathogenic *Escherichia coli* as assessed by multi-locus sequence analysis," Microbes Infect, 8: 1702-1713, 2006.

Justice et al., "Filamentation by *Escherichia coli* subverts innate defenses during urinary tract infection," PNAS, 103: 19884-19889, 2006.

Justice et al., "Maturation of intracellular *Escherichia coli* communities requires SurA," Infect Immun, 74: 4793-4800, 2006.

Langermann et al., "Prevention of mucosal *Escherichia coli* infection by FimH-adhesin-based systemic vaccination," Science, 276: 607-611, 1997.

Langermann et al., "Vaccination with FimH adhesin protects cynomolgus monkeys from colonization and infection by uropathogenic *Escherichia coli*," J Infect Dis, 181: 774-778, 2000.

Layton et al., "The effects of oral and combined parenteral/oral immunization against an experimental *Escherichia coli* urinary tract infection in mice," Clin Exp Immunol, 54: 305-312, 1983.

Mobley et al., "Uropathogenic *Escherichia coli* outer membrane antigens expressed during urinary tract infection," Infect Immun, 75: 3941-3949, 2007.

Mobley et al., "Pyelonephritogenic *Escherichia coli* and killing of cultured human renal proximal tubular epithelial cells: role of hemolysin in some strains," Infect Immun, 58: 1281-1289, 1990.

Mulvey et al., "Establishment of a persistent *Escherichia coli* reservoir during the acute phase of a bladder infection," Infect Immun, 69: 4572-4579, 2001.

O'Hanley et al., "Alpha-hemolysin contributes to the pathogenicity of piliated digalactoside-binding *Escherichia coli* in the kidney: efficacy of an alpha-hemolysin vaccine in preventing renal injury in the BALB/c mouse model of pyelonephritis," Infect Immun, 59: 1153-1161, 1991.

Ochman & Selander, et al., "Standard reference strains of *Escherichia coli* from natural populations," J Bacteriol, 157: 690-693, 1984.

Palaszynski et al., "Systemic immunization with conserved pilus-associated adhesins protects against mucosal infections," Dev Biol Stand, 92: 117-122, 1998.

Roberts et al., "Antibody responses and protection from pyelonephritis following vaccination with purified *Escherichia coli* PapDG protein," J Urol, 171: 1682-1685, 2004.

Rosen et al., "Detection of intracellular bacterial communities in human urinary tract infection," PLoS Med, 4:e329, 2007.

Russo et al., "A killed, genetically engineered derivative of a wild-type extraintestinal pathogenic *E. coli* strain is a vaccine candidate," Vaccine, 25: 3859-3870, 2007.

Russo et al., "The Siderophore receptor IroN of extraintestinal pathogenic *Escherichia coli* is a potential vaccine candidate," Infect Immun, 71: 7164-7169, 2003.

Schilling et al., "Effect of trimethoprim-sulfamethoxazole on recurrent bacteriuria and bacterial persistence in mice infected with uropathogenic *Escherichia coli*," Infect Immun, 70: 7042-7049, 2002.

Thumbikat et al., "Antigen-specific responses accelerate bacterial clearance in the bladder," J Immunol, 176: 3080-3086, 2006.

Uehling et al., "Decreased immunologic responsiveness following intensified vaginal immunization against urinary tract infection," J Urol, 143: 143-145, 1990.

Uehling et al., "Immunization against urinary tract infection with a multi-valent vaginal vaccine," J Urol, 146: 223-226, 1991.

Uehling et al., "Vaginal immunization against induced cystitis in monkeys," J Urol, 137: 327-329, 1987.

Uehling et al., "Vaginal immunization of monkeys against urinary tract infection with a multi-strain vaccine," J Urol, 151: 214-216, 1994.

International Search Report and Written Opinion for PCT Application No. PCT/US2010/034892, mailed Dec. 23, 2010.

\* cited by examiner

LIVE-ATTENUATED COMPOSITIONS FOR BACTERIAL INFECTIONS

The present application is a continuation of U.S. patent application Ser. No. 13/266,346, filed Dec. 23, 2011, now U.S. Pat. No. 8,709,444, which is a national phase application under 35 U.S.C. §371 of PCT International Application No. PCT/US2010/034892, filed on May 14, 2010, which claims priority to U.S. Provisional Patent Application Ser. No. 61/178,384, filed May 14, 2009, the entire disclosure of each of which is herein incorporated by reference in its entirety.

STATEMENT REGARDING GOVERNMENT FUNDING

This invention was made with government support under DK042648 awarded by the National Institutes of Health. The government has certain rights in this the invention.

FIELD OF THE INVENTION

The present invention relates to compositions and methods for disease treatment and prevention through administration of a live attenuated composition. In particular, the present invention provides compositions and methods for the treatment and prevention of urinary tract infection by administration of live attenuated compositions lacking O-antigen ligase activity.

BACKGROUND OF THE INVENTION

Urinary tract infection (UTI) is one of the most commonly acquired bacterial infections leading to a physician consultation. UTIs are estimated to account for 7 million office visits per year and 1 million visits to the emergency department, leading to an economic impact of $1.6 billion annually (Foxman (2002) Am J Med. 113 (Suppl 1A):5S-13S; herein incorporated by reference in its entirety). Uropathogenic *Escherichia coli* (UPEC) are the leading cause of UTI and account for up to 90% of uncomplicated infections (Foxman and Brown (2003) Infect. Dis. Clin. North Am. 17:227-41; herein incorporated by reference in its entirety). Antimicrobial therapy, the leading treatment for UTI, has become increasingly complicated by the rise of antimicrobial resistance among urinary tract pathogens. Furthermore, persistent and recurrent UTIs present a clinical challenge, given the absence of a widely protective and effective preventative therapy for UTI.

Vaccine design and development for the prevention and/or treatment of UPEC infection has been impeded by a limited understanding of the host immune responses during UTI. Characterizations of innate and adaptive immune responses to UPEC during UTI indicate that infection produces abundant pathogen-associated inflammatory responses. Several UPEC-targeted vaccine candidate strategies have been evaluated, including vaccines against pilus adhesins FimCH, PapDG and Dr adhesion and vaccines directed against non-adhesin UPEC virulence factors such as hemolysin and IroN (Foxman and Brown (2003) Infect. Dis. Clin. North Am. 17:227-41; Langermann et al. (2000) J Infect. Dis. 181:774-8; Langermann et al. (1997) Science 276:607-11; Palaszynski et al. (1998) Dev. Biol. Stand. 92:117-22; Roberts et al. (2004) J Urol. 171:1682-5; Hull et al. (2002) Infect. Immun. 70:6481-4; Goluszko et al. (2005) 73:627-31; Russo et al. (2003) Infect. Immun. 71:7164-9; O'Hanley et al. (1991) Infect. Immun. 59:1153-61; each herein incorporated by reference in their entireties). Additionally, limited success has been achieved through vaccination against UTI by using vaginal, nasal or oral administration of killed preparations of UPEC (Hopkins et al. (2007) J Urol. 177:1349-53; Layton and Smithyman (1983) Clin. Exp. Immunol. 54:305-12); Grischke and Ruttgers (1987) Urol. Int. 42:338-41; Uehling et al. (1994) 151:214-6; Uehling et al. (1991) J Urol. 146: 223-6; Uehling et al. (1990) J Urol. 143:143-5; Uehling et al. (1987) J Urol. 137:327-9; Russo et al. (2007) Vaccine 25:3859-70; each herein incorporated by reference in their entireties). A more systematic approach has been recently applied to identify potential vaccine antigens expressed in the outer membrane which provide protection against challenge after vaccination (Hagan and Mobley (2007) Infect. Immun. 75:2679-88; Alteri and Mobly (2007) Infect. Immun. 75:3941-9; each herein incorporated by reference in their entireties). Despite these efforts, no reliable vaccine strategy has been widely employed for UTI, indicating the need for alternative UTI vaccine strategies.

UPEC present further challenges to treatment and prevention. Intracellular invasion of and biofilm formation in host urothelial cells by UPEC strains has been demonstrated in both animal models and in human UTI patients (Garafalo et al. (2007) Infect. Immun. 75:52-60; Rosen et al. (2007) PLoS Med. 4:e329; Justice et al. (2006) PNAS 103:19884-9; Anderson et al. (2003) Science 301:105-7; each herein incorporated by reference in their entireties). These biofilm-type UPEC are more resistant to host clearance and may be more resistant to antimicrobial therapy (Justice et al. (2006) PNAS 103:19884-9; Mulvey et al. (2001) Infect. Immun. 69:4572-9; Schilling et al. (2002) Infect. Immun. 70:7042-9; each herein incorporated by reference in their entireties). Some have hypothesized that chronic colonization and recurrent UTI by UPEC could be due, in part, to the intracellular invasion and biofilm formation. Another possible explanation for recurrent UPEC infection is that deficiencies in host innate and/or adaptive immune responses prevent the development of lasting protective immunity to reinfection. Given these challenges, new strategies are warranted for the development of multifunctional approaches to UPEC vaccine design which bolster the immune response and eradicate intracellular bacterial reservoirs.

Accordingly, there is need in the art for improved methods and vaccines to prevent and treat bacterial infection, particularly urinary tract infection.

SUMMARY OF THE INVENTION

The present invention relates to compositions and methods for disease treatment, prevention, and study through administration of a composition that generates an immune response in subjects. In particular, the present invention provides compositions and methods for the treatment, prevention, and study of urinary tract infection and related states, conditions or symptoms (e.g., cystitis, urethritis, pyelonephritis) by administration of a composition with reduction or absence of O-antigen ligase function (e.g., O-antigen ligase activity, transcript, expression, protein level, protein stability) to a subject. The present invention further provides methods and compositions for the purpose of researching the prevention or treatment of urinary tract infection and related disease states (e.g., cystitis, urethritis, pyelonephritis) by administration of a live attenuated compositions with reduction or absence of O-antigen ligase function (e.g., O-antigen ligase activity, transcript, expression, protein level, protein stability) to a subject, without limitation to species of the subject.

In some embodiments, the composition is a live attenuated vaccine. In a preferred embodiment, the live attenuated composition is a bacterial strain. In some embodiments, the bacterial strain is a strain of uropathogenic *E. coli* (UPEC). In some embodiments, the bacterial strain is a strain of a species other than *E. coli*, including but not limited to *Proteus mirabilis, Pseudomonas aeruginosa, Enterocococcus* spp., *Klebsiella pneumonia, Proteus morganii*, and *Streptococcus faecalis*. In some embodiments, the UPEC strain used as a live attenuated composition is NU14. In some embodiments, the strain used as a live attenuated composition is derived from NU14. In some embodiments, the strain used as a live attenuated composition lacks, has a reduction in, or partially lacks an O-antigen moiety of lipopolysaccharide (LPS). In some embodiments, the strain used as a live attenuated composition lacks O-antigen ligase function (e.g., altered O-antigen ligase activity, transcript, expression, protein level, protein stability). In some embodiments, the reduction in O-antigen ligase function is achieved by reducing or suppressing O-antigen ligase activity. In some embodiments, the reduction in O-antigen ligase function is achieved by reducing the level of O-antigen ligase protein. In some embodiments, the reduction in O-antigen ligase function is achieved by altering O-antigen ligase protein activity or stability without limitation to means or mechanism of such alteration. In some embodiments, an agent is used to reduce O-antigen ligase activity. In some embodiments, an agent is used to reduce or alter the activity or presence of a protein required for the function of O-antigen ligase. In some embodiments, a reduction or elimination of O-antigen ligase activity occurs by virtue of a reduction in O-antigen ligase expression. In some embodiments, a reduction or elimination of O-antigen ligase function is achieved by reducing or eliminating the production of transcript encoding O-antigen ligase. In some embodiments, the reduction or elimination of O-antigen ligase transcript is achieved by gene silencing (Barrangou et al. (2007) Science 315: 1709-1712; U.S. patent application Ser. No. 11/596,176; each herein incorporated by reference in their entireties).

In some embodiments, the reduction in O-antigen ligase expression is achieved by mutating, disrupting, or otherwise rendering nonfunctional a gene encoding a protein with O-antigen ligase function. In some embodiments, the gene encoding O-antigen ligase is waaL (also known as rfaL). In some embodiments, the bacterial strain used as a live attenuated composition is NU14ΔwaaL. In some embodiments, the reduction in O-antigen ligase function is achieved by mutating, disrupting, or otherwise rendering nonfunctional a gene encoding a protein interacting with O-antigen ligase. In some embodiments, the reduction in O-antigen ligase expression is achieved by mutating, disrupting, or otherwise rending nonfunctional a gene encoding a regulatory protein or nucleic acid required for the expression of a gene encoding a protein with O-antigen ligase function. In some embodiments, the reduction in O-antigen ligase expression is achieved by mutating, disrupting, or otherwise rending nonfunctional a gene encoding a regulatory protein or nucleic acid required for the expression of a gene encoding a protein with O-antigen biosynthesis function. In some embodiments, the reduction in O-antigen ligase expression is achieved by mutating, disrupting, or otherwise rending nonfunctional a gene encoding a regulatory protein or nucleic acid required for the expression of a gene encoding a protein with lipopolysaccharide biosynthesis function. In some embodiments, the reduction in O-antigen ligase expression is achieved by mutating, disrupting, or otherwise rending nonfunctional a gene encoding a regulatory protein or nucleic acid required for the expression of a gene encoding a protein with lipid A biosynthesis function. In some embodiments, the reduction in O-antigen ligase expression is achieved by mutating, disrupting, or otherwise rending nonfunctional a gene encoding a regulatory protein or nucleic acid required for the expression of a gene encoding a protein with core oligosaccharide biosynthesis function. In some embodiments, one or more other genes or proteins that influence peptidoglycan biosynthesis or altered or regulated (e.g., AmpG, or Alr).

In some embodiments, a composition (e.g., vaccine) is formulated for effective administration through inclusion of additional agents (e.g., excipients, adjuvants, preservatives, stabilizing agents, salts, buffering agents, immunogenic agents).

The present invention provides a method for treating or preventing bacterial infection in a subject by administering a composition that induces an immune response in a subject. The invention is not limited by any particular route or means of administration, nor by the nature of the induced immune response. In some embodiments, the bacterial infection is a urinary tract infection (UTI) or related state, condition, or symptom (e.g., cystitis, urethritis, pyelonephritis). In some embodiments, the subject is at risk for suffering from a UTI or related state, condition, or symptom (e.g., cystitis, urethritis, pyelonephritis). In some embodiments, the subject is a human. In some embodiments, the subject is a non-human species (e.g., mouse, rat, canine, feline, bird, bovine, caprine, or any other species used as livestock, veterinary, zoological, or model research animal purposes). In some embodiments, the subject has been diagnosed as suffering from UTI. In some embodiments, the subject is at risk for UTI due to one or more of the following conditions: underlying structural, medical, or neurologic disease; having prior history of UTIs; diaphragm contraceptive use; diabetes; lack of circumcision in males; catheterization; neurogenic bladder or bladder diverticulum; postmenopausal state in women; bladder or uterine prolapse in women; high urine glucose content; defective host immune factors; loss of estrogen; loss of lactobacilli; urethral infection; prostatic infection in men; prostatic obstruction and/or subsequent instrumentation in men.

In some embodiments, the method for treating or preventing bacterial infection in a subject involves administering a bacterial composition described herein.

In some embodiments, the composition used for treating or preventing bacterial infection is formulated for effective administration through inclusion of additional agents (e.g., adjuvants, preservatives, stabilizing agents, salts, buffering agents, immunogenic agents). The method for treating or preventing bacterial infection is not limited to any particular dose or treatment regime. The composition may be administered at least once; twice; three times; four times; 5-10 times; 10-20 times; 20-100 times; 100 times or more. The method is not limited by the duration of time between repetitive administrations of the composition. The method is not limited by the duration of time between administration of the composition and challenge or exposure to a pathogenic agent. The duration of time may be 0 days; 1 day; 2 days; 3 days; 4 days; 5 days; 5-7 days; 1-2 weeks; 2-4 weeks; 4-8 weeks; 8-10 weeks; 10-31 weeks; 31-52 weeks; 1-5 years; 5-10 years; 10-20 years; 20-50 years; 50-100 years or more. In some embodiments, the subject is tested for the presence of a urinary tract infection prior to administration of the composition. In some embodiments, the subject is not tested for the presence of a urinary tract infection prior to the administration of the composition. In some embodiments, the subjected is tested for urinary tract infection following administration of the composition. Such testing may be conducted less than one day, 1-2 days, 2-4 days, 4-6 days, 6-8 days, 8-10 days, 10-15 days, 15-20 days, 20-30 days, 30 or more days prior to administration of the composition.

In some embodiments, the method for treating or preventing bacterial infection in a subject involves co-administration of a composition with treatments or therapies directed towards urinary tract infection. In some embodiments, the composition is administered in advance of treatments or therapies directed towards UTI. In some embodiments, the composition is administered simultaneously with treatments or therapies directed towards UTI. In some embodiments, the composition is administered after administration of treatments or therapies directed towards UTI. In some embodiments, the composition is administered in combination with a bladder analgesic agent (e.g., phenazopyridine (Pyridium®. Urogesic®), antipyretic agents, or general analgesic agents (e.g., acetaminophen (Tylenol®). In some embodiments, the composition is administered while the subject is undergoing treatment with IV fluid. In some embodiments, the composition is administered prior to catheterization. In some embodiments, the composition is administered simultaneously with catheterization. In some embodiments, the composition is administered after the subject undergoes catheterization.

In certain embodiments, the present invention provides a method of treating bacterial infection in a subject comprising administering to a subject a live attenuated composition lacking or reduced in O-antigen ligase function. In some embodiments, the subject is experiencing a urinary tract infection. In some embodiments, the subject is at risk of experiencing a urinary tract infection. In some embodiments, the subject is human. In some embodiments, the lack or reduction in O-antigen ligase function is promoted by altering characteristics such as O-antigen ligase activity, O-antigen ligase protein level, O-antigen ligase protein stability, O-antigen ligase transcript, O-antigen ligase transcript stability, and functional O-antigen ligase-encoding gene. In some embodiments, the O-antigen ligase-encoding gene is waaL. In some embodiments, the live attenuated composition comprises a strain of *E. coli*. In some embodiments, the strain of *E. coli* is uropathogenic. In some embodiments, the live attenuated composition is NU14 ΔwaaL.

In certain embodiments, the present invention provides a composition comprising a live attenuated bacterial strain lacking or reduced in O-antigen ligase function. In certain embodiments, the lack or reduction in O-antigen ligase function is promoted by altering characteristics such as O-antigen ligase activity, O-antigen ligase protein level, O-antigen ligase protein stability, O-antigen ligase transcript, O-antigen ligase transcript stability, and functional O-antigen ligase-encoding gene. In certain embodiments, the bacterial strain is a strain of *E. coli*. In certain embodiments, the *E. coli* strain is uropathogenic. In certain embodiments, the bacterial strain is NU14 ΔwaaL.

DEFINITIONS

Figure 1:
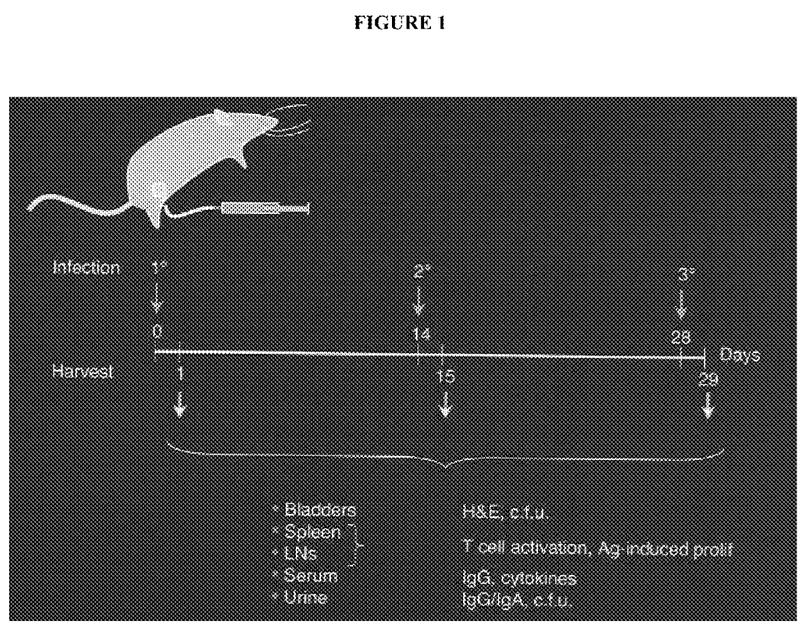
FIG. 1 shows a mouse model of urinary tract infection.
Figure 2:
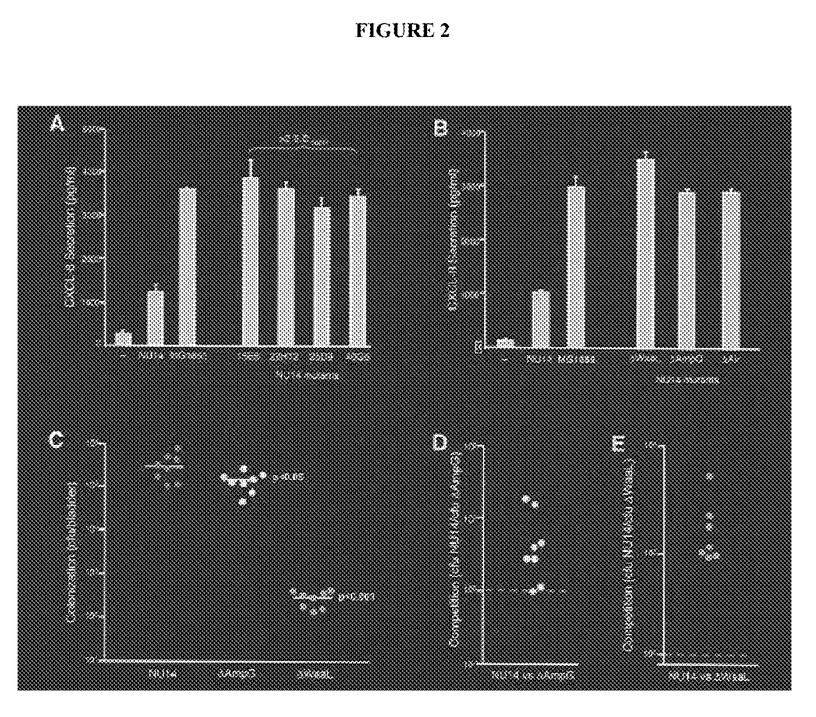
FIG. 2 shows the lack of urovirulence of NU14-ΔwaaL. A, CXCL-8 secretion (pg/ml) elicited by NU14, MG1655, or NU14 mutants. B, CXCL-8 secretion (pg/ml) elicited by NU14, MG1655, ΔWaaL, ΔAmpG, or ΔAlr. C, Colonization (cfu/bladder) occurring upon infection by NU14, ΔAmpG, or ΔWaaL. D, Competition study between NU14 and ΔAmpG. E, Competition study between NU14 and ΔWaaL.
Figure 3:
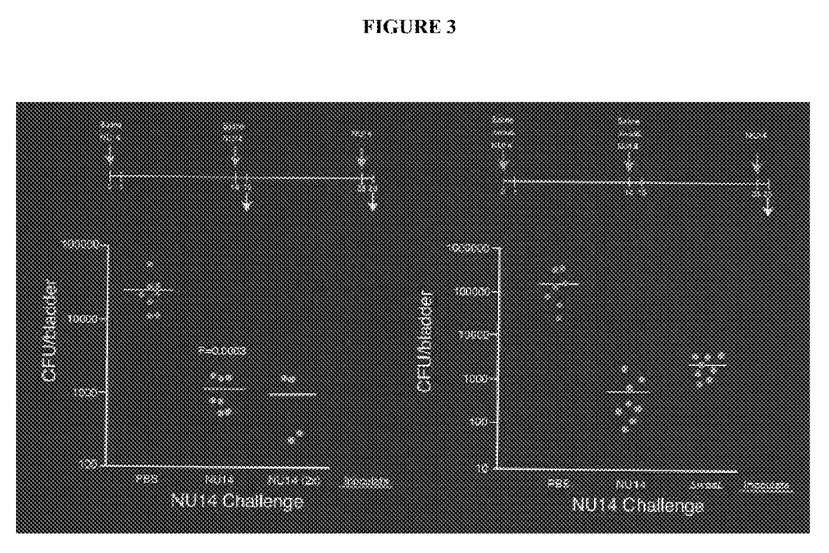
FIG. 3 shows that NU14-ΔwaaL elicits a protective response against subsequent bladder infection by NU14. Upper panel, infection protocols corresponding to the colonization data directly below. The data indicate that prior inoculation with NU14-ΔwaaL induces greater than 100-fold increased protection as compared to prior inoculation with NU14.
Figure 4:
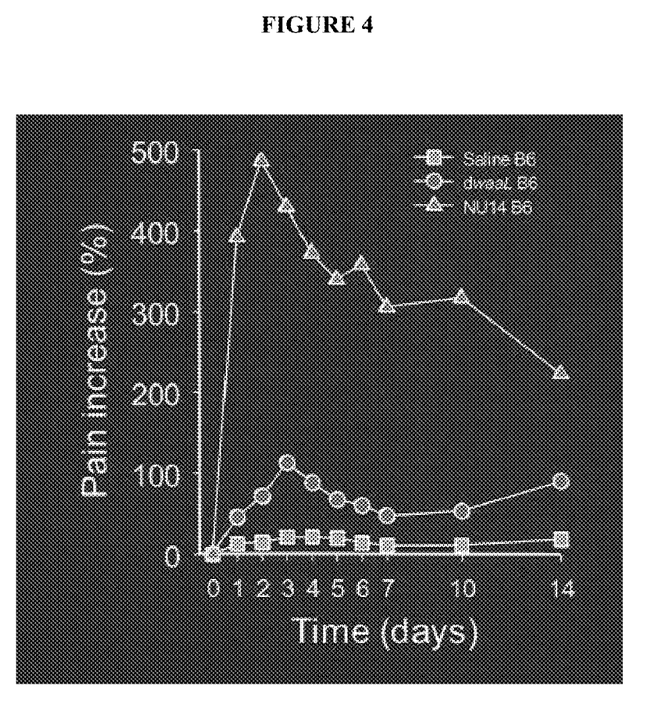
FIG. 4 shows that NU14 ΔwaaL fails to induce pelvic pain in a murine model, whereas NU14 induces significant pelvic pain. Methods for pelvic pain assay were as in Rudick et al (2007) Am J Physiol Regul Integr Comp Physiol. 293: R1191-8 (herein incorporated by reference in its entirety.)

To facilitate understanding of the invention, a number of terms are defined below.

As used herein, the term "urinary tract infection" is known in the art and refers to infection of the kidney, ureter, bladder, or urethra. The related condition cystitis is caused by bacteria entering the urethra and then the bladder, leading to inflammation and infection in the lower urinary tract. The related condition pyelonephritis is an infection of the kidney and/or the ureters. Urinary tract infection may affect the upper urinary tract, the lower urinary tract, or both. Urinary tract infection may be chronic or acute.

As used herein, the term "live attenuated vaccine" is known in the art and refers to a vaccine containing live micro-organisms that have been cultivated under conditions that disable their virulent properties or which contains closely-related but less virulent organisms to evoke a broad immune response.

As used herein, the term "O-antigen ligase function" refers to the process of ligation of O polysaccharide (O-antigen) and lipid A-core oligosaccharide, without regard to the mechanism by which such ligation occurs. Ligation may occur by action of a single enzyme, or by action of more than one enzyme, either working in concert or sequentially.

As used herein, the terms "subject" and "patient" refer to any animal, such as a mammal like a dog, cat, bird, livestock, and preferably a human.

The term "culture medium" is recognized in the art, and refers generally to any substance or preparation used for the cultivation of living cells.

The terms "defective" or "mutated" as used herein, with regard to a gene or gene expression, means that the gene is not a wild-type gene and that the organism does not have a wild-type genotype and/or a wild-type phenotype. The defective gene, genotype or phenotype may be the consequence of a mutation in that gene, or of a gene that regulates the expression of that gene (e.g., transcriptional or post-transcriptional), such that its normal expression is disrupted or extinguished. "Disrupted gene expression" is intended to include both complete inhibition and decreased gene expression (e.g., as in a leaky mutation), below wild-type gene expression levels.

The term "Gram-negative bacteria" is recognized in the art, and refers generally to bacteria that do not retain Gram stain (e.g., the deposition of a colored complex between crystal violet and iodine). In an exemplary Gram stain, cells are first fixed to a slide by heat and stained with a basic dye (e.g., crystal violet), which is taken up by all bacteria (i.e., both Gram-negative and Gram-positive). The slides are then treated with an iodine-KI mixture to fix the stain, washed with acetone or alcohol, and finally counterstained with a paler dye of different color (e.g., safranin) Gram-positive organisms retain the initial violet stain, while Gram-negative organisms are decolorized by the organic solvent and hence show the counterstain. Exemplary Gram-negative bacteria and cell lines include, but are not limited to, *Escherichia* spp., *Shigella* spp., *Salmonella* spp., *Campylobacter* spp., *Neisseria* spp., *Haemophilus* spp., *Aeromonas* spp., *Francisella* spp., *Yersinia* spp., *Klebsiella* spp., *Bordetella* spp., *Legionella* spp.,

*Corynebacteria* spp., *Citrobacter* spp., *Chlamydia* spp., *Brucella* spp., *Pseudomonas* spp., *Helicobacter* spp. and *Vibrio* spp.

The term "mutant Gram-negative bacteria", as used herein, includes Gram-negative bacteria of the invention that have been mutated one or more times in, for example, one or more of the waaL, waaK, waaZ, waaY, waaR, waaO, waaB, waaS, waaP, waaG, waaQ, waaA, or waaC genes, or any other biosynthetic, processing, or trafficking gene thereby producing O-antigen, core oligosaccharide, or lipid A. The waa operon has previously been referred to as the rfa operon (i.e., rfaL, rfaK, rfaZ, rfaY, rfaR, rfaO, rfaB, rfaS, rfaP, rfaG, rfaQ, rfaQ, rfaC).

An "immunogenic portion of a molecule" refers to a portion of the molecule that is capable of eliciting an immune reaction against the molecule in a subject.

As used herein, the term "portion" when used in reference to a sequence (e.g., an amino acid sequence of a protein, a nucleic acid sequence of a gene) represents any amount of the referenced sequence (e.g., 0.001%, 0.1%, 1%, 10%, 30%, 50%, 75%, 80%, 85%, 90%, 95%, 98%, 99.999% of an amino acid sequence or nucleic acid sequence).

The term "modulation" as used herein refers to both up-regulation (i.e., activation or stimulation (e.g., by agonizing or potentiating)) and down-regulation (i.e., inhibition or suppression (e.g., by antagonizing, decreasing or inhibiting)). The term "inducible" refers in particular to gene expression which is not constitutive but which takes place in response to a stimulus (e.g., temperature, heavy metals or other medium additive).

The term "non-human subject" includes any animal that can be treated or used in testing the present invention, including mammals such as non-human primates, rodents, sheep, dogs, cows, pigs, chickens, as well as amphibians, reptiles, etc. Preferred non-human animals are selected from the primate family or rodent family (e.g., rat and mouse).

The term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs and as applicable to the embodiment being described, single (sense or antisense) and double-stranded polynucleotides.

The term "pharmaceutically acceptable" means a material that is not biologically or otherwise undesirable, i.e., the material may be administered to an individual along with the selected compound without causing any undesirable biological effects or interacting in a deleterious manner with any of the other compounds of the pharmaceutical composition in which it is contained.

As used herein, the term "transfection" means the introduction of a nucleic acid (e.g., via an expression vector) into a recipient cell by nucleic acid-mediated gene transfer. "Transformation", as used herein, refers to a process in which a cell's genotype is changed as a result of the cellular uptake of exogenous DNA or RNA. In an illustrative embodiment, a transformed cell is one that expresses a mutant form of the waaL gene. A transformed cell can also be one that expresses a nucleic acid that interferes with the expression of a waaL gene or any other O-antigen, core oligosaccharide, or lipid A biosynthetic, processing, or trafficking gene.

As used herein, the term "transgene" means a nucleic acid (e.g., a mutant waaL gene or any other biosynthetic, processing, or trafficking gene, or an antisense transcript thereto) that has been introduced into a cell. A transgene could be partly or entirely heterologous, i.e., foreign, to the transgenic animal or cell into which it is introduced, or, can be homologous to an endogenous gene of the organism or cell into which it is introduced, but which is designed to be inserted, or is inserted, into the animal or cell's genome in such a way as to alter the genome of the cell into which it is inserted. A transgene can also be present in a cell in the form of an episome.

The term "treating" a subject for a condition or disease, as used herein, is intended to encompass curing, as well as ameliorating at least one symptom of the condition or disease.

The term "vector" refers to a nucleic acid molecule, which is capable of transporting another nucleic acid to which it has been linked. Vectors capable of directing the expression of genes to which they are operatively linked are referred to herein as "expression vectors." The term "expression system" as used herein refers to an expression vector under conditions whereby an mRNA may be transcribed and/or an mRNA may be translated into protein, structural RNA, or other cellular component. The expression system may be an in vitro expression system, which is commercially available or readily made according to techniques known in the art, or may be an in vivo expression system, such as a eukaryotic or prokaryotic cell containing the expression vector. In general, expression vectors of utility in recombinant DNA techniques are often in the form of "plasmids" which refer generally to circular double stranded DNA loops that, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and are well known in the art or which become known in the art subsequently hereto (e.g., cosmid, phagemid and bacteriophage vectors).

DETAILED DESCRIPTION OF THE INVENTION

New strategies are needed for the development of multi-functional approaches to UPEC vaccine design which bolster the immune response and eradicate intracellular bacterial reservoirs. Experiments conducted during the course of development of some embodiments of the present invention tested whether increased stimulation of host innate immune responses by attenuated UPEC mutants may increase known protective adaptive immune responses to enhance protection or clearance during UTI. A derivative of NU14, NU14 ΔwaaL, was constructed which has a targeted deletion of the gene that encodes the O-antigen ligase required for joining the variable O-antigen onto the lipid A-core component of lipopolysaccharide during biosynthesis (Billips et al. (2008) Infect. Immun. 76:3891-3900; herein incorporated by reference in its entirety). This mutant is severely attenuated in a mouse model of UTI and stimulates enhanced urothelial and innate immune responses during infection (Billips et al. (2008) Infect. Immun. 76:3891-3900; herein incorporated by reference in its entirety). As shown by experiments conducted during the development of embodiments of the present invention, NU14 ΔwaaL inoculation protects mice against subsequent challenge with either wild-type NU14 or a panel of diverse clinical UPEC isolates.

Stimulation of proinflammatory cytokine secretion and up-regulation of costimulatory molecules on antigen presenting cells bridge the innate and adaptive immune response to pathogens during infection. It was contemplated that mutants of NU14 which stimulate enhanced innate immune responses in potential antigen presenting cells (APCs) may, in turn, enhance protective adaptive responses. It was found that NU14 ΔwaaL significantly enhanced macrophage IL-6 secretion relative to the wild-type NU14. Though NU14 ΔwaaL is much less virulent and cleared from the urinary tract rapidly in the mouse model of UTI (see Billips et al. (2008) Infect. Immun. 76:3891-3900; herein incorporated by reference in its entirety), in experiments conducted during the course of development of some embodiments of the present invention, NU14 ΔwaaL immunization proved equally effective at conferring protection against NU14 challenge. While the present invention is not limited to any mechanism of action and an understanding of the mechanism of action is not necessary to practice the invention, NU14 ΔwaaL may be more immunogenic, possibly due to the lack of O-antigen on LPS. In fact, O-antigen interferes with toll-like receptor 4 recognition of the lipid A component of LPS, thereby reducing the induction of proinflammatory signaling pathways (Backhed et al. (2003) Microbes Infect. 5:1057-63; Backhed et al. (2001) Cell Microbiol. 3:153-8; each herein incorporated by reference in their entireties). Russo et al. demonstrated that vaccination with a formalin-killed ExPEC strain deficient in capsule and lacking O-antigen increased host antibody production to bacterial antigens and augmented antibody-mediated bactericidal activity by neutrophils (Russo et al. (2007) Vaccine 25:3859-70; herein incorporated by reference in its entirety). Recent studies indicate that UPEC modulate host innate immune responses at early stages of infection (Billips et al. (2007) Infect. Immun. 75:5353-60; Bhushan et al. (2008) J. Immunol. 180:5537-47; Hunstad et al. (2005) Infect. Immun. 73:3999-4006; Hilbert et al. (2008) Microbes Infect. 10:114-21; Cirl et al. (2008) Nat. Med. 14:399-406; each herein incorporated by reference in their entireties). Modulation of these innate immune responses by UPEC may also influence the magnitude or nature of adaptive immune response during UTI at the level of APC activity. Alternatively, UPEC may also modulate adaptive immune responses directly through unidentified mechanisms.

The limited success of monovalent UTI vaccines based upon known virulence factors highlights the need for diverse UTI vaccine strategies. Monovalent UTI vaccine candidates have previously been identified based on two criteria: the prevalence of an antigen among UPEC strains and the demonstrated role in virulence in experimental UTI. These approaches have demonstrated immunogenicity and protection in murine models of UTI (Langermann et al. (2000) J Infect. Dis. 181:774-8; Langermann et al. (1997) Science 276:607-11; Palaszynski et al. (1998) Dev. Biol. Stand. 92:117-22; Roberts et al. (2004) J Urol. 171:1682-5; Hull et al. (2002) Infect. Immun. 70:6481-4; Goluszko et al (2005) 73:627-31; Russo et al. (2003) Infect. Immun. 71:7164-9; O'Hanley et al. (1991) 59:1153-61; each herein incorporated by reference in their entireties), but have yet to demonstrate effectiveness in human trials. Since UPEC derive from four distinct groups of *E. coli* (Ochman and Selander (1984) J Bacteriol. 157:690-3; Johnson et al. (2006) Microbes Infect. 8:1702-13; each herein incorporated by reference in their entireties), it is possible that monovalent vaccines fail to stimulate immune responses that are sufficiently broad to protect against genetically diverse uropathogens. Thus, live-attenuated UTI vaccines are more likely to generate broadly protective immunity against diverse UPEC strains because of polyvalency. NU14 ΔwaaL represents such a live-attenuated UTI vaccine.

Because genetically diverse *E. coli* cause urinary tract infection, an attenuated vaccine that is based upon the most prevalent phylogenetic group of UPEC is most likely to successfully confer protection against the majority of UTI. The NU14 strain utilized in the illustrative examples herein resides within the B2 clonal group, the *E. coli* clonal group most frequently responsible for UTI (Johnson et al. (2001) J Infect. Dis. 183:1508-17; herein incorporated by reference in its entirety). Importantly, NU14 ΔwaaL immunization confers cross-protection against challenge with multiple B2 group UPEC isolates and group A and D strains that are less frequently associated with UTI's, but are uropathogenic nonetheless. Ideal vaccines should also protect against ascending colonization of the upper urinary tract by UPEC. NU14 ΔwaaL vaccination reduced ascending kidney colonization in 4 of 5 clinical isolates tested, including the three ECOR pyelonephritis isolates utilized, and prevented any detectable colonization from 2 of the 5 UPEC isolates. Because the live-attenuated vaccine utilizes a whole cell preparation, the immunity generated by NU14 ΔwaaL instillation is likely polyvalent and more resistant to the genetic variability of the diverse pool of potential UPEC strains.

The clinical significance of persistence of colonization and intracellular invasion by UPEC is relevant. It is possible that intracellular UPEC play important roles in recurrence of UTI (Justice et al. (2006) PNAS 103:19884-9; Anderson et al. (2003) Science 301:105-7; Mulvey et al. (2001) Infect. Immun. 69:4572-9; Schilling et al. (2002) Infect. Immun. 70:7042-9; Justice et al. (2006) Infect. 1 mm. 74:4793-4800; each herein incorporated by reference in their entireties), and therefore any potential UPEC vaccine therapy should effectively reduce or eliminate these bacterial reservoirs. In experiments conducted during the course of development of some embodiments of the present invention, NU14 ΔwaaL did not persistently colonize the mouse bladder, suggesting that this strain may be deficient in intracellular invasion of urothelium and/or is unable to form IBC's to avoid clearance from the bladder. Furthermore, NU14 ΔwaaL vaccination prevents persistent UPEC colonization upon challenge with wild-type NU14, suggesting a sterilizing immunity that eradicates intracellular UPEC.

Additional mutations of NU14ΔwaaL that further enhance recognition of conserved pathogen-associated microbial patterns (PAMPs), such as deletion of ampG or alr, are contemplated to enhance the efficacy of NU14 ΔwaaL as a UTI vaccine (Billips et al. (2008) Infect. Immun. 76:3891-3900; herein incorporated by reference in its entirety). A UPEC vaccine or immune response inducing composition may be used for a number of purposes, including: as a prophylactic to prevent initial or recurrent UTI, and as a therapeutic vaccine given to resolve chronic UPEC colonization. The live-attenuated NU14 ΔwaaL compositions are contemplated to find use for both of these applications, as well as others. Given that O-antigen is common among Gram-negative pathogens, ΔwaaL mutants provide a general strategy for attenuated-live vaccines against diverse human and veterinary pathogens.

Gram-negative bacilli include (1) the Enterobacteriaceae, a family which comprises many important pathogenic genera, (2) *Vibrio, Campylobacter* and *Helicobacter* genera, (3) opportunistic organisms (e.g., *Pseudomonas, Flavobacterium*, and others) and (4) *Haemophilus* and *Bordetella* genera. The Gram-negative bacilli are the principal organisms found in infections of the abdominal viscera, peritoneum, and urinary tract, as well secondary invaders of the respiratory tracts, burned or traumatized skin, and sites of decreased host resistance. Currently, they are the most frequent cause of life-threatening bacteremia. Examples of pathogenic Gram-negative bacilli are *E. coli* (diarrhea, urinary tract infection, meningitis in the newborn), *Shigella* species (dysentery), *Salmonella typhi* (typhoid fever), *Salmonella typhimurium* (gastroenteritis), *Yersinia enterocolitica* (enterocolitis), *Yersinia pestis* (black plague), *Vibrio cholerae* (cholera), *Campylobacter jejuni* (enterocolitis), *Helicobacter jejuni* (gastritis; peptic ulcer), *Pseudomonas aeruginosa* (opportunistic infections including burns, urinary tract, respiratory tract, wound infections, and primary infections of the skin, eye and ear), *Haemophilus influenzae* (meningitis in children, epiglottitis, otitis media, sinusitis, and bronchitis), and *Bordetella pertussis* (whooping cough). *Vibrio* is a genus of motile, Gram-negative rod-shaped bacteria (family Vibrionaceae). *Vibrio cholerae* causes cholera in humans; other species of *Vibrio* cause animal diseases. *E. coli* colonize the intestines of humans and warm blooded animals, where they are part of the commensal flora, but there are types of *E. coli* that cause human and animal intestinal diseases. They include the enteroaggregative *E. coli* (EaggEC), enterohemorrhagic *E. coli* (EHEC), enteroinvasive *E. coli* (EIEC), enteropathogenic *E. coli* (EPEC) and enterotoxigenic *E. coli* (ETEC). Uropathogenic *E. coli* (UPEC) cause urinary tract infections. There are also neonatal meningitis *E. coli* (NMEC). Apart from causing similar infections in animals as some of the human ones, there are specific animal diseases including: calf septicemia, bovine mastitis, porcine oedema disease, and air sac disease in poultry.

The pathogenic bacteria in the Gram-negative aerobic cocci group include *Neisseria, Moraxella (Branhamella)*, and the *Acinetobacter*. The genus *Neisseria* includes two important human pathogens, *Neisseria gonorrhoeae* (urethritis, cervicitis, salpingitis, proctitis, pharyngitis, conjunctivitis, pharyngitis, pelvic inflammatory disease, arthritis, disseminated disease) and *Neisseria meningitides* (meningitis, septicemia, pneumonia, arthritis, urethritis). Other Gram-negative aerobic cocci that were previously considered harmless include *Moraxella (Branhamella) catarrhalis* (bronchitis and bronchopneumonia in patients with chronic pulmonary disease, sinusitis, otitis media) which has recently been shown to be an common cause of human infections.

I. Administration Routes and Pharmaceutical Compositions

The present invention further provides pharmaceutical and research compositions (e.g., comprising a vaccine for prevention or treatment of bacterial infection described herein). The pharmaceutical and research compositions of the present invention may be administered in a number of ways depending upon whether local or systemic treatment is desired and upon the area to be treated. Administration may be topical, pulmonary (e.g., by inhalation or insufflation of powders or aerosols, including by nebulizer; intratracheal, intranasal, epidermal and transdermal), intravesical, oral, or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids, semisolids, monophasic compositions, multiphasic compositions (e.g., oil-in-water, water-in-oil), foams microsponges, liposomes, nanoemulsions, aerosol foams, polymers, fullerenes, and powders (see, e.g., Taglietti et al. (2008) Skin Ther. Lett. 13:6-8). Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carder compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

The compositions of the present invention may include excipients known in the art. Examples of excipients used for vaccine formulation such as adjuvents, stabilizers, preservatives, and trace products derived from vaccine manufacturing processes include but are not limited to: Aluminum Hydroxide, Amino Acids, Benzethonium Chloride, Formaldehyde or Formalin, Inorganic Salts and Sugars, Vitamins, Asparagine, Citric Acid, Lactose, Glycerin, Iron Ammonium Citrate, Magnesium Sulfate, Potassium Phosphate, Aluminum Phosphate, Ammonium Sulfate, Casamino Acid, Dimethyl-beta-cyclodextrin, 2-Phenoxyethanol, Bovine Extract, Polysorbate 80, Aluminum Potassium Sulfate, Gelatin, Sodium Phosphate, Thimerosal, Sucrose, Bovine Protein, Lactalbumin Hydrolysate, Formaldehyde or Formalin, Monkey Kidney Tissue, Neomycin, Polymyxin B, Yeast Protein, Aluminum Hydroxyphosphate Sulfate, Dextrose, Mineral Salts, Sodium Borate, Soy Peptone, MRC-5 Cellular Protein, Neomycin Sulfate, Phosphate Buffers, Polysorbate, Bovine Albumin or Serum, DNA, Potassium Aluminum Sulfate, Amorphous Aluminum Hydroxyphosphate Sulfate, Carbohydrates, L-histidine, Beta-Propiolactone, Calcium Chloride, Neomycin, Ovalbumin, Potassium Chloride, Potassium Phosphate, Sodium Phosphate, Sodium Taurodeoxycholate, Egg Protein, Gentamicin, Hydrocortisone, Octoxynol-10, α-Tocopheryl Hydrogen Succinate, Sodium Deoxycholate, Sodium Phosphate, Beta-Propiolactone, Polyoxyethylene 910, Nonyl Phenol (Triton N-101, Octoxynol 9), Octoxinol-9 (Triton X-100), Chick Kidney Cells, Egg Protein, Gentamicin Sulfate, Monosodium Glutamate, Sucrose Phosphate Glutamate Buffer Calf Serum Protein, Streptomycin, Mouse Serum Protein, Chick Embryo Fibroblasts, Human Albumin, Sorbitol, Sodium Phosphate Dibasic, Sodium Bicarbonate, Sorbitol, Sucrose, Potassium Phosphate Monobasic, Potassium Chloride, Potassium Phosphate Dibasic, Phenol, Phenol Red (Phenolsulfonphthalein), Amphotericin B, Chicken Protein, Chlortetracycline, Ethylenediamine-Tetraacetic Acid Sodium (EDTA), Potassium Glutamate, Cell Culture Media, Sodium Citrate, Sodium Phosphate Monobasic Monohydrate, Sodium Hydroxide, Calcium Carbonate, D-glucose, Dextran, Ferric (III) Nitrate, L-cystine, L-tyrosine, Magnesium Sulfate, Sodium Hydrogenocarbonate, Sodium Pyruvate, Xanthan, Peptone, Disodium Phosphate, Monosodium Phosphate, Polydimethylsilozone, Hexadecyltrimethylammonium Bromide Ascorbic Acid, Casein, Galactose, Magnesium Stearate, Mannitol, Hydrolyzed Porcine Gelatin, Freund's emulsified oil adjuvants (complete and incomplete), Arlacel A, Mineral oil, Emulsified peanut oil adjuvant (adjuvant 65), *Corynebacterium granulosum*-derived P40 component, Lipopolysaccharide, *Mycobacterium* and its components, Cholera toxin, Liposomes, Immunostimulating complexes (ISCOMs), Squalene, and Sodium Chloride.

Dosing may be dependent on severity and responsiveness of the condition or disease state to be treated, with the course of treatment lasting from several days to several months, or until a cure is effected or a diminution of the condition or disease state is achieved, or until optimal immune response is achieved, or until optimal protection against future infection is achieved. Optimal dosing schedules can be calculated from measurements of drug accumulation in the body of the patient. The administering professional (e.g., physician) can easily determine optimum dosages, dosing methodologies and repetition rates. Optimum dosages may vary depending on the relative potency of the agent (e.g., molecule, oligonucleotide, siRNA, antibody, virus, microbe, cell, bacterial cell), and can generally be estimated based on $EC_{50s}$ found to be effective in in vitro and in vivo animal models or based on the examples described herein. In general, dosage is from 0.01 μg to 100 g per kg of body weight, and may be given once or more daily, weekly, monthly or yearly. The administering professional can estimate repetition rates for dosing based on measured residence times and concentrations of the drug in bodily fluids or tissues. Following successful treatment, it may be desirable to have the subject undergo maintenance therapy to prevent the recurrence of the disease state, wherein the treatment (e.g., molecule, siRNA or antibody, virus, microbe, cell, bacterial cell) is administered in maintenance doses, ranging from 0.01 μg to 100 g per kg of body weight, once or more daily, to once every 20 years.

In experiments conducted during the course of the development of embodiments of the present invention, the NU14 ΔwaaL was shown to act as a live attenuated vaccine for the prevention of urinary tract infection. The present invention is not limited to a particular dose, administration route, or administration regime to a subject. The vaccine may be administered at least once; twice; three times; four times; 5-10 times; 10-20 times; 20-100 times. The method is not limited by the duration of time between each repetition of vaccine administration. The method is not limited by the duration of time between administration of the vaccine and challenge or exposure to a pathogenic agent. The duration of time may be 0 days; 1 day; 2 days; 3 days; 4 days; 5 days; 5-7 days; 1-2 weeks; 2-4 weeks; 4-8 weeks; 8-10 weeks; 10-31 weeks; 31-52 weeks; 1-5 years; 5-10 years; 10-20 years; 20-50 years; 50-100 years.

EXPERIMENTAL

The following examples are provided in order to demonstrate and further illustrate certain embodiments and aspects of the present invention and are not to be construed as limiting the scope thereof.

Example I

This example describes the materials and methods used for Example II.

Bacterial Strains and Culture.

The *E. coli* strains used in this study were cultured at 37° C. in LB-Miller broth under static conditions for 48 hours to promote the surface expression of type 1 pili (Old and Duguid (1970) J Bacteriol. 103:47-56; herein incorporated by reference in its entirety). MG1655 is a K-12 strain fecal isolate and NU14 (O18:K1:H7) is a streptomycin-resistant B2 clonal group *E. coli* strain isolated from a cystitis patient (Hultgren et al. (1986) Infect. Immun. 54:613-20; Blattner et al. (1997) Science 277:1453-74; each herein incorporated by reference in their entireties). NU14-1 is a chloramphenicol-resistant fimH mutant of NU14, and is defective in type 1 pili-mediated adherence (Langermann et al. (1997) Science 276L607-11; herein incorporated by reference in its entirety). Strain NU14 ΔwaaL contains a targeted deletion of waaL, the gene which encodes O-antigen ligase for lipopolysaccharide biosynthesis (Hultgren et al. (1986) Infect. Immun. 54:613-20; Folkesson et al. (2005) Cell Microbiol. 7:147-55; each herein incorporated by reference in their entireties). CFT073, a well characterized UPEC strain, was originally isolated from a patient with pyelonephritis (Mobley et al. (1990) Infect. Immun. 58:1281-9; herein incorporated by reference in its entirety). The clinical *E. coli* UTI isolates from the ECOR panel, ECOR 11, ECOR 14, ECOR 40, ECOR 50, ECOR 60, ECOR 64 were obtained from Dr. James Johnson (Ochman and Selander (1984) J Bacteriol. 157:690-3; Johnson et al. (2001) J Infect. Dis. 183:897-906; each herein incorporated by reference in their entireties). All antibiotics were added at the following concentrations; 100 μg/ml streptomycin, 30 μg/ml chloramphenicol and 100 μg/ml kanamycin.

Cell Lines and Culture.

RAW 264.7 mouse macrophage cells were cultured in RPMI (MediaTech) with 10% fetal bovine serum (HyClone) in a 5% $CO_2$/37° C. atmosphere and penicillin/streptomycin (MediaTech).

Cytokine Secretion Assays.

RAW 264.7 cells were cultured in 6-well plates in medium without antibiotics prior to infection with bacteria. The bacterial inoculates were prepared by centrifugation at 10,000×g for five minutes. The bacterial pellets were resuspended in sterile PBS and the bacterial concentration was determined by measuring absorbance at 600 nm. The appropriate volume of each bacterial suspension, to a final MOI of 50:1 (bacterial: cell), was added to cell culture medium and then added to the cell cultures. IL-6 secretion in culture supernatants was determined following 4 hours of treatment. Where noted, media were supplemented with 10 ng/ml recombinant mouse TNF-α (Millipore) or 1 μg/ml LPS O55:B5 (Sigma) as controls. Culture supernatants were collected, cleared by centrifugation, and assayed for IL-6 by ELISA (R&D Systems).

Vaccination, Bacterial Colonization, and Challenge Experiments.

For the vaccination (inoculation) and bacterial challenge experiments, 6-8 week old female C57BL/6 mice were instilled while under isoflurane (Baxter Inc.) anesthesia via transurethral catheter with a volume of 10 μl containing 1×10$^8$ cfu (colony forming units) of the indicated bacterial strain or 10 μl sterile phosphate-buffered saline. Vaccinated mice received two inoculations each using NU14 or NU14 ΔwaaL or were instilled with 10 μl of PBS fourteen days apart (Day 1 and Day 14). Two weeks after vaccination mice were challenged by infection via instillation with NU14 or the indicated bacterial strain. The duration of the vaccine's effectiveness was determined by challenging mice by infection with NU14 2, 4 and 8 weeks after vaccination. To determine bacterial colonization following infection, bladders were harvested at the indicated time post infection (24 hours or 14 days), homogenized, and plated onto EMB-agar containing the appropriate antibiotics.

Statistical Analysis.

Results were analyzed with the student T-test or a one-way ANOVA analysis followed by Bonferroni's Multiple Comparison Test using Prism software from GraphPad Inc. Differences between groups of data were considered significant for P values less than or equal to 0.05.

TABLE 1

Bacterial strains and plasmids used in this study.

| Plasmids | Characteristics | Reference |
| --- | --- | --- |
| pFLAG-MAC | IPTG inducible expression for N-terminal FLAG fusion proteins | Sigma-Aldrich Co. |
| pwaaL | Derivative of pFLAG-MAC expressing WaaL | Billips et al. (2008) Infect. Imm. 76:3891-3900 |
| Bacterial Strains | | |
| NU14 | Clinical UPEC isolate (urine) | Hultgren et al. (1986) Infect. Immun. 54:613-20 |
| NU14 ΔwaaL | Derived from NU14, targeted deletion of waaL | Billips et al. (2008) Infect. Imm. 76:3891-3900 |
| NU14-1 type 1 pili- | Derived from NU14, insertion into fimH, defective mediated adherence | Langermann et al. (1997) Science 276:607-11 |
| CFT073 | Clinical UPEC isolate (urine), ECOR panel | Mobley et al. (1990) 58:1281-9 |
| ECOR 11 | Clinical UPEC isolate (urine), ECOR panel | Ochman et al. (1984) J Bacteriol. 157:690-3 |
| ECOR 14 | Clinical UPEC isolate (urine), ECOR panel | Ochman et al. (1984) J Bacteriol. 157:690-3 |
| ECOR 40 | Clinical UPEC isolate (urine), ECOR panel | Ochman et al. (1984) J Bacteriol. 157:690-3 |
| ECOR 50 | Clinical UPEC isolate (urine), ECOR panel | Ochman et al. (1984) J Bacteriol. 157:690-3 |
| ECOR 60 | Clinical UPEC isolate (urine), ECOR panel | Ochman et al. (1984) J Bacteriol. 157:690-3 |
| ECOR 64 | Clinical UPEC isolate (urine), ECOR panel | Ochman et al. (1984) J Bacteriol. 157:690-3 |

TABLE 2

Characteristics of bacterial strains used in vaccine challenge.

| Bacterial Strains | Clinical Origin | Clonal Group | Pap Pili | Type 1 Pili | IL-8 Suppression[1] |
| --- | --- | --- | --- | --- | --- |
| NU14 | Cystitis | B2 | + | + | + |
| CFT073 | Pyelonephritis | B2 | + | + | +[2] |
| ECOR 11 | Cystitis | A | + | + | + |
| ECOR 14 | Pyelonephritis | A | − | + | − |
| ECOR 40 | Pyelonephritis | D | + | + | + |
| ECOR 50 | Pyelonephritis | D | + | + | + |
| ECOR 60 | Cystitis | B2 | + | + | + |
| ECOR 64 | Cystitis | B2 | − | + | + |

[1]Suppression of TNFα-mediated IL-8 secretion from urothelial cells (Billips et al (2007) Infect. Immun. 75:5353-60)
[2]Unpublished observation and Cirl et al. (2008) Nat. Med. 14:399-406

Example II

NU14 ΔwaaL Stimulates Enhanced IL-6 Secretion from RAW 264.7 Murine Macrophages

The targeted deletion of the waaL gene of UPEC strain NU14 resulted in enhanced innate immune responses from human urothelial cell cultures during infection, including increased stimulation of IL-8 and IL-6 secretion (Billips et al. (2008) Infect. Immun. 76:3891-3900; herein incorporated by reference in its entirety). In order to examine whether NU14 ΔwaaL enhanced cytokine responses of potential APCs, the levels of IL-6 secretion from culture supernatants of the mouse macrophage line RAW 264.7 treated with LPS, NU14, NU14-1 or NU14 ΔwaaL were compared. Treatment with LPS, a well known stimulator of macrophage cytokine secretion, induces significantly higher levels of IL-6 secretion from the macrophage cultures relative to untreated cells (196.3±34.38 vs. 46.33±5.812 ng/ml, respectively, P<0.001). NU14 ΔwaaL enhanced IL-6 secretion from human urothelial cells and infection with NU14 ΔwaaL stimulated significantly higher levels of IL-6 secretion than infection with NU14 (244.3±38.37 vs. 57.67±2.517 ng/ml, respectively, P<0.001). Adherence via type 1 pili did not affect IL-6 secretion from macrophages, as a mutant strain deficient in type I pili-mediated adherence (NU14-1) and the wild-type strain elicited equivalent levels of IL-6 secretion.

Enhanced stimulation of IL-8 secretion from urothelial cell cultures due to deletion of waaL can be complemented through expression of the waaL gene from a plasmid (Billips et al. (2008) Infect. Immun. 76:3891-3900; herein incorporated by reference in its entirety). In order to determine whether enhanced stimulation of IL-6 secretion from other cell types could also be complemented, the secretion of IL-6 from macrophages treated with either NU14 ΔwaaL/pFLAG (empty vector control) or NU14 ΔwaaL/pwaaL was compared. Both NU14 ΔwaaL and the empty-vector control strain NU14 ΔwaaL/pFLAG stimulated higher levels of IL-6 secretion from RAW 264.7 cell cultures than cells treated with the mutant strain carrying a copy of the waaL gene, NU14 ΔwaaL/pwaaL (302.7±24.19, 324.0±29.46 vs. 85.33±37.00 ng/ml, respectively, P<0.001). These data show that altered structure of LPS lacking intact O-antigen is the factor responsible for the increase in IL-6 secretion from murine macrophages during infection with NU14 ΔwaaL, although an understanding of the mechanism is not needed to practice the invention and the invention is not limited to any particular mechanism of action.

Like several other clinical UPEC isolates, NU14 suppresses cytokine secretion from many urothelial cell types stimulated by other non-suppressor E. coli strains or by treatment with purified LPS or TNFα (Billips et al. (2007) 75:5353-60; Bhushan et al. (2008) J Immunol. 180:5537-47; Hunstad et al. (2005) Infect. Imun. 73:3999-4006; Hilbert et al. (2008) Microbes Infect. 10:114-21; Cirl et al. (2008) Nat. Med. 14:399-406; each herein incorporated by reference in their entireties). TNFα treatment stimulated IL-6 secretion from RAW 264.7 mouse macrophage cultures relative to untreated cultures (1046±14.19 vs. 257.3±7.424 ng/ml, respectively, P<0.001). In the presence of NU14, TNFα induced significantly lower levels of IL-6 secretion than TNFα treatment alone (338.7±10.41 vs. 1046±14.19 ng/ml, respectively, P<0.001), suggesting that NU14 suppress TNFα-mediated IL-6 secretion from murine macrophages. Also, NU14 ΔwaaL induced significantly less IL-6 secretion in the presence of TNFα than cells treated with TNFα alone (620.0±75.75 vs. 1046±14.19 ng/ml, respectively, P<0.001). Yet, NU14 ΔwaaL still elicited higher levels of IL-6 secretion than NU14 in the presence of TNFα (338.7±10.41 vs. 620.0±75.75 ng/ml, respectively, P<0.01). This suggests that suppression of TNFα-mediated IL-6 secretion in macrophage cultures by NU14 ΔwaaL is incomplete. These findings indicate that the TNFα-suppressive activity by NU14 is partially dependent of the O-antigen ligase activity encoded by waaL, although an understanding of the mechanism is not needed to practice the invention and the invention is not limited to any particular mechanism of action.

Vaccination with NU14 ΔwaaL Protects from Subsequent Challenge with UPEC in Murine UTI.

NU14 infection generates adaptive immune responses which protect mice upon reinfection (Thumbikat et al. (2006) J Immunol. 176:3080-6; herein incorporated by reference in its entirety). Inoculation with NU14 elicits protective adaptive immune responses which can be transferred to naïve hosts via serum or purified T cells (Thumbikat et al. (2006) J Immunol. 176:3080-6; herein incorporated by reference in its entirety). In order to determine if inoculation with the attenuated UPEC strain NU14 ΔwaaL could also induce protective adaptive immune responses, groups of mice twice were inoculated via instillation into the bladder with NU14, NU14 ΔwaaL or saline (mock-vaccinated). Upon subsequent challenge with NU14, mice vaccinated with either NU14 or NU14 ΔwaaL had significantly less bladder colonization than mock-vaccinated mice (584.4±633.8, 2552±1279 vs. 169000±138102 cfu/bladder, respectively, P<0.01). Single inoculations with NU14 produce a protective effect from subsequent challenge, however a single inoculation with NU14 ΔwaaL was less effective than inoculation with NU14. These data, in addition to the previous observation that NU14 ΔwaaL is severely deficient in bladder colonization in an acute murine model of UTI, show that NU14 ΔwaaL provides a live-attenuated vaccine to prevent UTI due to UPEC (Billips et al. (2008) Infect. Immun. 76:3891-3900; herein incorporated by reference in its entirety).

NU14 ΔwaaL Confers Durable Protection.

In order to determine the durability of protection conferred by NU14 ΔwaaL, vaccinated mice were challenged with NU14 at 2, 4 and 8 weeks after inoculation. Overall, vaccination with NU14 ΔwaaL reduced bladder colonization after infection with NU14 (P<0.003). Challenge at two weeks post-infection revealed that bladder colonization was significantly reduced in vaccinated animals compared to mock-vaccinated controls (1938±609.2 vs. 217500±64750 cfu/bladder, P<0.0001). Challenge with NU14 four weeks after vaccination resulted in mean bladder colonization in the vaccinated group significantly lower than the mock vaccinated control group (7819±4039 vs. 338800±207300 cfu/bladder, P<0.0001). Vaccination with NU14 ΔwaaL also diminished bladder colonization relative to saline-instilled controls upon challenge with NU14 eight weeks post-inoculation (13780±2594 vs. 43130±14940 cfu/bladder, P<0.0002). Over time, bladder colonization after NU14 challenge in mock-vaccinated mice significantly decreased as indicated by the reduced colonization at 8 weeks compared to colonization 2 weeks after mock-vaccination (43130±14940 vs. 217500±64750 cfu/bladder, P<0.001). This may indicate increasing age-dependent resistance to UPEC infection in the murine model of UTI or resistance through exposure to E. coli in animal housing. Also, the mean bladder colonization in the vaccinated groups displays a rising trend, indicating that the vaccine may have reduced efficacy beyond 8 week post-inoculation. Ultimately, inoculation with NU14 ΔwaaL stimulates a protective response exhibiting durability against UPEC challenge.

Vaccination Protects Mice from Persistent Bladder Colonization by UPEC.

Several studies have shown that UPEC can persistently colonize the mouse urinary tract following an acute infection. This colonization may involve both vegetative and biofilm UPEC which chronically colonize the mouse bladder for months following infection. A live-attenuated UPEC-based vaccine should ideally, therefore, also exhibit a severely diminished capacity for chronic colonization of the urinary tract. Previous studies indicated that bladder colonization by wild-type NU14 decreases sharply following instillation, and by Day 5 post-infection a low but persistent level of colonization is reached. In order to determine whether NU14 ΔwaaL was capable of persistent bladder colonization, mice were infected with either NU14 or NU14 ΔwaaL and bacterial colonization was quantified 14 days after infection. NU14 infection resulted in detectable chronic colonization (121.2±180.6 cfu/bladder) in 4 of 5 mice, while NU14 ΔwaaL-infected mice had no detectable bladder colonization at two weeks. Also, vaccination with either NU14 or NU14 ΔwaaL protected mice from persistent colonization with NU14 compared to mice instilled with saline only (65.22±81.39, 19.10±38.78 vs. 592.3±462 cfu/bladder, respectively, P<0.001). Furthermore, a comparison of the vaccinated animals showed that 6 of the 10 mice vaccinated with NU14 ΔwaaL had no detectable colonization fourteen days after challenge, while only 2 of 9 mice vaccinated with NU14 had no detectable bladder colonization. Therefore NU14 ΔwaaL vaccination is more effective at protecting against persistent UTI infection, chronic bladder colonization by NU14 upon challenge, perhaps due to enhanced adaptive immune responses which prevent the development or persistence of UPEC reservoirs, although an understanding of the mechanism is not needed to practice the invention and the invention is not limited to any particular mechanism of action.

NU14 ΔwaaL Protects Against Diverse UPEC Isolates.

The genetic diversity of UPEC isolates suggests that a UTI vaccine of high clinical value should confer protection against challenge with multiple E. coli strains. Representative UPEC strains isolated from patients with either cystitis or pyelonephritis were identified. Together, these strains also represented additional members of the B2 clonal group and members of the A and D clonal groups (Table 2). Mice were infected via instillation with each of the chosen ECOR isolates, ECOR 11, ECOR 14, ECOR 40, ECOR 50, ECOR 60, ECOR 64, NU14 and CFT073 and determined bladder and kidney colonization levels 24 hours post-infection. NU14 and CFT073 colonized both the bladders and kidneys of infected mice. ECOR 11 and ECOR 60 failed to efficiently colonize the murine urinary tract, so these two strains were excluded from further study. The other ECOR isolates, 14, 40, 50 and 60 all colonized both the bladder and kidneys of infected mice and were thus useful for the study of the range of the protection acquired through vaccination using NU14 ΔwaaL. No correlation was found between clinical origin, clonal group classification or presence pap fimbriae (identified by PCR) and colonization of the murine urinary tract; however those strains that most efficiently colonized the bladder also efficiently colonized the kidneys (e.g., NU14, CFT073, and ECOR 40).

The breadth of the protection generated by NU14 ΔwaaL vaccination in mice by quantifying bladder and kidney colonization after challenge with NU14, CFT073, ECOR 14, ECOR 40, ECOR 50 and ECOR 60, relative to mock-vaccinated mice were evaluated. Vaccination decreased the mean levels of bladder colonization of all 6 UPEC strains compared to the mock-vaccinated group 24 hours post infection (P<0.001). Vaccination also lowered mean kidney colonization of NU14, ECOR 14, ECOR 40 and ECOR 50 (P<0.001). Although mean kidney colonization was not significantly lower in vaccinated mice upon challenge with ECOR 64, inoculation with NU14 ΔwaaL did reduce the number of animals with detectable kidney colonization (2/8) compared to the saline control group (4/8). Overall, vaccination using NU14 ΔwaaL proved highly effective for increasing host resistance to challenge from a broad range of clinically relevant UPEC isolates.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A solid or semi-solid composition formulated for therapeutic administration to a subject via a suppository comprising:
   i) a sterilized carrier formulation selected from: an oily base, gelatin, and polyoxyethylene; and
   ii) a live attenuated uropathogenic E. coli strain with a non-functional or deleted waaL gene such that said live attenuated uropathogenic E. coli strain is lacking O-antigen ligase function.

2. The composition of claim 1, wherein said lack or reduction in O-antigen ligase function is promoted by altering characteristics selected from among the group consisting of O-antigen ligase activity, O-antigen ligase protein level, O-antigen ligase protein stability, O-antigen ligase transcript, and O-antigen ligase transcript stability.

3. The composition of claim 1, wherein said uropathogenic E. coli strain is NU14 ΔwaaL.

4. The composition of claim 1, further comprising said adjuvant.

* * * * *